US008750960B2

(12) United States Patent
Boyce et al.

(10) Patent No.: US 8,750,960 B2
(45) Date of Patent: Jun. 10, 2014

(54) PROCESS FOR SELECTING BONE FOR TRANSPLANTATION

(75) Inventors: Todd M. Boyce, Matawan, NJ (US); Stephen N. Mercadante, Middletown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1759 days.

(21) Appl. No.: 10/519,202

(22) PCT Filed: Jul. 17, 2003

(86) PCT No.: PCT/US03/22340
§ 371 (c)(1),
(2), (4) Date: Aug. 8, 2005

(87) PCT Pub. No.: WO2004/008943
PCT Pub. Date: Jan. 29, 2004

(65) Prior Publication Data
US 2006/0100498 A1 May 11, 2006

Related U.S. Application Data

(60) Provisional application No. 60/397,236, filed on Jul. 19, 2002.

(51) Int. Cl.
*A61B 5/05* (2006.01)
(52) U.S. Cl.
USPC ........ 600/407; 623/16.11; 600/425; 600/427; 606/167
(58) Field of Classification Search
USPC ...................................... 623/16.11
See application file for complete search history.

(56) References Cited

U.S. PATENT DOCUMENTS

| 4,436,684 | A | * | 3/1984 | White | 264/138 |
| 5,741,215 | A | * | 4/1998 | D'Urso | 600/407 |
| 6,192,329 | B1 | * | 2/2001 | Rider et al. | 703/6 |
| 6,451,059 | B1 | * | 9/2002 | Janas et al. | 623/23.51 |
| 6,458,144 | B1 | * | 10/2002 | Morris et al. | 606/179 |
| 6,459,948 | B1 | * | 10/2002 | Ateshian et al. | 700/117 |
| 6,932,842 | B1 | * | 8/2005 | Litschko et al. | 623/16.11 |
| 6,944,518 | B2 | * | 9/2005 | Roose | 700/117 |
| 6,988,015 | B1 | * | 1/2006 | Schopf et al. | 700/98 |
| 7,103,233 | B2 | * | 9/2006 | Stearns | 382/289 |

(Continued)

OTHER PUBLICATIONS

A Morphometric Comparison of Trabecular Structure of Human Ilium Between Microcomputed Tomography and Conventional Histomorphometry / Calcified Tissue International / vol. 61, No. 6 / Dec. 1997.*

(Continued)

*Primary Examiner* — Unsu Jung
*Assistant Examiner* — Joel Lamprecht
(74) *Attorney, Agent, or Firm* — Sorell Lenna & Schmidt LLP (57) ABSTRACT

A procedure for determining a plan for cutting a bone sample for use as an implant provides scanning the bone with a CT scanning system to provide slice images of the bone. The scanning system then determines the cortical or cancellous bone dimensions and density of the bone. Determining such dimensions and density permits accurate planning and preparation of an implant graft that is correlated to the predetermined plan without waste of bone through cutting test specimens to determine the bone parameters. Other images techniques that provide slice images are also disclosed.

36 Claims, 7 Drawing Sheets

(56) References Cited

U.S. PATENT DOCUMENTS

| | | | |
|---|---|---|---|
| 7,217,266 B2* | 5/2007 | Anderson et al. | 606/12 |
| 2002/0139147 A1* | 10/2002 | Janas et al. | 65/376 |
| 2002/0191823 A1* | 12/2002 | Wehrli et al. | 382/128 |
| 2003/0045936 A1* | 3/2003 | Angelucci et al. | 623/17.11 |
| 2003/0198660 A1* | 10/2003 | Janas et al. | 424/423 |
| 2003/0236473 A1* | 12/2003 | Dore et al. | 600/587 |
| 2006/0093645 A1* | 5/2006 | Janas et al. | 424/423 |

OTHER PUBLICATIONS

Uchiyama et al., "A Morphometric Comparsion of Trabecular Structure of Human Ilium Between Microcomputed Tomography and Conventional Histomorphometry", Dec. 1997, Calcified Tissue International, vol. 61, No. 6.*

International Search Report, Apr. 22, 2004.

* cited by examiner

Cancellous Spacer Bone Mineral Density-Comparison of XCT 2000 vs. Dry Density Measurements.

FIG. 4

Cancellous Spacer Bone Mineral Density-Comparison of XCT 2000 vs. Load at Yield Measurements

Cortical Wall Measurements Prior to Reaming

FIG. 7

Cortical Wall Measurements Prior to Reaming

PROCESS FOR SELECTING BONE FOR TRANSPLANTATION

This application is a national stage entry of PCT/US03/22340, filed Jul. 17, 2003, which claims priority based on provisional application Ser. No. 60/397,236, filed Jul. 19, 2002, the contents of which are incorporated herein by reference in their entirety.

This invention relates to procedures for selecting bone for transplant implants, and more, particularly, to non-destructively generating an accurate, three-dimensional image of a bone, determining bone parameters such as cortical thickness, interior diameter (ID) and outer diameter (OD) dimensions, density of the donor cortical and cancellous regions of the bone, developing a implant production plan or work order from the determined parameters and then cutting the bone into the predetermined implant configurations.

Bone is collected from a donor, prepared using a number of standard techniques, and cut, milled, ground, crushed, machined, or otherwise prepared into the forms that are used for tissue transplantation at a skeletal site. For certain prepared forms, the geometric and dimensional measurements of cortical bone are critical to obtaining a structurally sound bone transplant product. Implants prepared using the method of the invention can be used in a variety of skeletal repair procedures, including but not limited to spinal interbody fusion, defect repair, onlay grafting, long bone fusion, segmental grafting, and trauma repair.

For many implant forms, the selection of high-strength cancellous bone with specific density and quality is critical. Standard practice requires that bones from a donor be cut and measured using calipers before, or during processing, in order to assess the suitability of the donor for a particular implant product. This measuring approach requires a destructive cut for assessment. This can be costly, inefficient and the data are difficult to interpret. Also, if the grafts need to be prepared aseptically, the assessment cut must be made in a clean room environment, typically immediately prior to processing. Not all bones examined in this manner are suitable for processing in to implants and this results in delays and added cost, because clean rooms must be decontaminated and sterilized prior to each bone examination and technicians must work on bones which may be determined unsuitable after cutting.

Current radiographic methods employ fluoroscopic techniques, digital X-ray, or other procedures, which may permit the assessment of the bone dimensions in a non-destructive manner, but these methods are often inaccurate because of projection and focus effects. Projection effects generate errors in the image of an object being visualized because the beam angle of the emitting source spreads outward form the source, through the object and then on to the recording medium. This spread angle of the beam creates an image that is distorted from the original object. This projection effect is greater as the distances between the object being visualized and the center of the emitting source increases. Additionally, focus effects are generated by these imaging methods because only a small portion the object being visualized lies directly perpendicular to the recording medium plane. Focus effects can distort any portion of an object that is not in direct contact with the recording medium because of the volume through which the beam must pass before contacting the recording medium. This means that only regions of a bone, which are in direct contact with the recording medium, can be assessed accurately for wall thickness. This is not a satisfactory method to precisely determine the thickness of any bone since bone morphology and density can vary widely. Another problem with these approaches is the difficulty in determining the accurate position of the film plane in the image and correlating the image to such planes.

These obstacles make it impossible to determine, in advance, an accurate assessment of the yield that might be expected from the bone. This has often forced implant manufacturers to make decisions about tolerances, dimensions, and shapes based upon the best information available. Usually, that consisted of the experience, impressions and opinions of those knowledgeable about the process. This has at times provided implant templates that might have been improved and low yields of desirable implants from donor bone.

There is an ongoing need for the collection of accurate information about what implant geometries can consistently be prepared from various donor bones. There also exists a demand for reliable quantitative information about implants generated from a bone so that future decisions about suitable implant cutting plans may be optimized, waste may be reduced and the demand for particular implants can be met.

The present inventors recognize a need for a non-destructive reliable procedure for assessing bone parameters, which will identify bone suitable for transplant grafts. This invention relates to generating a accurate, three-dimensional image of a bone, preferably using quantitative computed tomography, to accurately assess thickness of cortical bone and bone mineral density for the generation of suitable implants.

Quantitative computed tomography has been used in the prior art, to evaluate bone quality in living patients, with the goal of making therapeutic interventions to reduce the risk of a fracture. This approach has also been used in the laboratory by bone researchers to estimate the structural strength of long bones in bending or torsion. The present invention differs from these uses in that it assesses bone in a screening or triage step for suitability prior to being cut into final graft implant forms.

A process for evaluating donor bone suitability for implant preparation, according to the present invention comprises imaging a bone using a three-dimensional imaging scan at one or more sites of the bone; measuring the bone parameters from the scan image; assessing the bone's suitability for fabrication into implants based on the measured parameters and generating a work plan for the cutting of implants. Suitable final configurations for which the bone might be assessed include but are not limited to; the implants described in U.S. Pat. Nos. 5,728,159, 5,814,084, 5,868,749, 6,025,538, 6,200,347, 6,261,586, 6,371,988, and 6,398,811.

This process for selecting bone may be used as an initial screening test, part of a larger bone selection protocol, or a final product test method to determine critical attributes compared to related pre-determined release specifications of an implant.

In one aspect, the imaging step comprises producing the image by computed tomography; in another aspect, producing the image step comprises producing the image by peripheral computed tomography; in another aspect, the imaging step comprises producing the image by magnetic resonance imaging; and in still another aspect, the producing the image step comprises producing the image by gamma-ray computed tomography. While these are examples, any imaging method that produces bone images of suitable dimensional accuracy is envisioned by this invention.

According to a further aspect, a process for evaluating donor bone suitability for implant preparation, comprises imaging the bone using a three-dimensional imaging method at one or more sites on the bone; generating morphometric measurements; extrapolating from morphometric measurements to dimensions at another skeletal site on the same or another bone; and determining the bone's suitability for implant geometries. For example, after scanning a distal radius (or other bone and location) the morphometric measurements may be extrapolated to determine the suitability of the medial radius, femur or other long bone. In a further aspect, a process for evaluating donor bone suitability for implant preparation comprises non-destructively assessing cortical thickness at one or more pre-selected sites of the bone.

In a further aspect, a computer-generated model that is based on historic osteometric data from a population of previously scanned bones may be used to generate the acceptance and cutting criteria for the bone being scanned. The scanned bone is compared to a stored population of bone morphometric measurements and its suitability for implants determined, based on the performance of previously scanned bones that are similar in morphometric measurements. Ideally, the computer program would then generate implant cutting specifications or a work plan for the scanned bone based on how implants were cut from similar bones in the past. In a further aspect of the invention a scalable model based on morphometric measurements for a given bone type could be used to map any cutting plan to bones of various sizes. Preferably a scan of the entire bone would not be needed but two or three scans of selected positions of the bone could be made and compared to the stored models for that bone type. The implant cutting specifications could then be mapped to the new bone or scaled up or down to fit variations in size and morphology from bone to bone.

Additionally the computer program could be used to mark the bone or otherwise identify where the cuts should be made. These specifications could then be used to manually prepare implants from the bone by a technician using standard cutting tools such as hand, band and table saws or preferably could be utilized in the automated (computer assisted or guided) cutting of implants. An automated cutting plan can be used to identify a tool path that minimizes loss and waste of bone. Automated cutters include but are not limited to robotic routers, laser cutters, water jets, laminated object manufacturing, computer assisted machining or other Computer Aided Design (CAD) fabrication methods.

The historical osteometric data are dynamic and therefore the computer program would preferably continue to store, analyze and update the historical archive of morphometric measurements to provide increasingly more accurate estimations of a bone's suitability for making various implants. In a further aspect of the invention, the computer program may be linked to implant orders and inventory so that the implants made from a bone meet the specific demand and reduce waste.

In a further aspect, the bone can be measured to within about +/−1.0 mm accuracy, preferably to within +/−0.5 mm accuracy, more preferably to within +/−0.1 mm accuracy, still more preferably to within +/−0.01 mm accuracy and most preferably to within +/−0.005 mm accuracy.

The invention now will be described with respect to the drawings, wherein.

DEFINITIONS

Computed Tomography—reconstruction of the three-dimensional structure of an object using projections of the object from multiple angles % of Length—the measurement position as determined by the overall length of the tissue, beginning from the most superior end of the bone.

Implant Configuration—the layout template comprising the number, type and specific geometries of implants which will be cut from bone.

Implant Cutting Plan—a production plan, work order cutting specification or a descriptive summary of the implants to be obtained from the bone, which provides the information necessary to manufacture implants from a given bone or part thereof. The implant cutting plan, production plan, work order, or cutting specification may define the types and sizes of implants, all implant geometries for manufacturing the implants, and the quantity of each type of implant that can be produced from a given bone. It is based on three dimensional morphometric measurements, which are free from the distortion inherent in two dimensional morphometric measurement techniques. The implant cutting plan, etc. may be a list, or it may be more detailed, to the point of including release specifications, donor information or specific locations from which implants will be obtained. The implant cutting plan, production plan, work order, or cutting specification may be generated by a computer after a bone is scanned. This cutting plan will increase the yield of implants from a bone when compared to previous plans based upon two-dimensional analysis, manual measurements with calipers and interpretation of implant tolerances, dimensions, and shapes by those conducting the process.

Morphometric measurement—This is defined as the measurement of the shape of an object through the use of physical and dimensional measurements which when taken together, define the shape (morphology) and structure. Morphological measurements allow screening, suitability assessments, and population characterization of shapes that would be otherwise indescribable.

Slice—the image section of an object being scanned and recorded during a single projection of the imaging process.

Sterile—having been treated by a terminally sterilizing step, e.g. irradiation with gamma rays, or procured and processed using sterile surgical recovery, storage and processing techniques.

Osteometric—measurement of bones and the information that can be obtained from them.

A three-dimensional imaging modality, particularly peripheral quantitative computed tomography (pQCT), is used to evaluate skeletal geometry of a bone of interest and make selections of a bone to be formed into a transplant graft based upon cross sectional information at one or more sites along the length of a long bone. Preferably, in the present examples, the instrument performing the peripheral CT scanning is model XCT 2000 peripheral CT scanner as provided by Norland Medical Systems, Inc. Other scanning instruments may also be used according to a given implementation. The disclosed procedure utilizes peripheral quantitative computed tomography (PQCT) for example employing the Norland Medical Systems, XCT 2000.

The measurement accuracy provided by the pQCT XCT 2000 of the imaged femur shaft is believed to approximate closely what is actually cut and measured. This instrument provides point measurement thickness of cortical bone and average thickness for the entire bone. It also provides bone density values for the imaged bone. The instrument produces images and calculations as programmed.

The bone mineral density provided by the pQCT XCT 2000 instrument of the imaged grafts (referred also as implants) through a sterile package is correlated with present density measurement and biomechanical yield strength. This could be used for quality control purposes to confirm the quality of the implant after processing and cutting. Also, the bone mineral density could be used in the whole bone to identify regions of sufficient strength to cut.

The slice data for the imaged femur shaft is three-dimensional in that it provides a cross sectional area over a given thickness measurement of a bone being imaged. The slices may be 0.2 mm, 2.0 mm or 2.2 mm, or any other thickness allowable under the controlling software of the CT system. The slice thickness is limited only by the system resolution and the scan time requirements. It should be understood that as technology improves, scan times will decrease and higher resolutions at slices less than 0.2 mm would be possible. The generated data permit an implant cutting plan to be established which details the implant type and expected quantity that will closely approximate or exactly specify the actual output cut from the bone tissue that is imaged and correlated with the 3D reconstruction output from the pQCT XCT 2000. Parameters which may be measured include: area, hole area, standard area count, perimeter, centroid X and Y, Z-position, width, length and height, orientation, breadth, fiber length, fiber breadth, shape factor, elongated form factor, inner radius, outer radius, mean radius, equivalent radius, equivalent spheroid volume, equivalent prolate volume, equivalent oblate volume, equivalent sphere surface area, average gray value, total gray value, optical integrated density, integrated optical density, intensity center X and Y, radial dispersion, texture difference moment; texture inverse difference moment, optical density variance, optical density relative low/medium or high areas, optical density relative low/medium or high amounts, optical density relative low/medium or high distances, and others including over may elliptical Fourier parameters to assist in defining shape analysis patterns.

Figure 1:
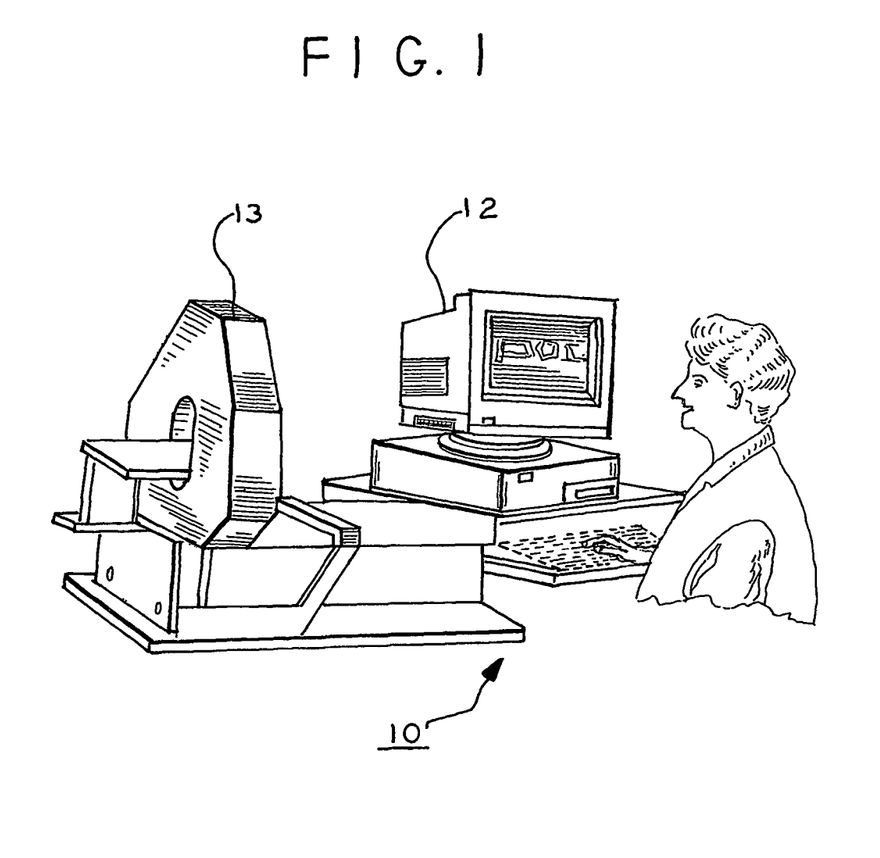
FIG. 1 is a perspective view of a computed tomography (CT) scanning system that is commercially available for scanning peripheral objects, and is used to practice a preferred form of the process according to an embodiment of the present invention.

In FIG. 1, the peripheral CT scanner system 10 comprises a preprogrammed computer 12 and an imaging apparatus 13 as provided for example by Norland Medical Systems, model PQCT XCT 2000. This system employs a scanner using a detector comprising 12 CdTe semiconductors and scan tube as provided by Toshiba. The focal spot size is 0.7 mm with an anode angle of 12 degrees. The anode current is less than 0.3 mA with an anode voltage of about 58 kV. The X-ray energy is about 48 keV. The system uses a filter of 250 urn Cu. The system provides images of the scanned bone cross sections, histograms of data acquired and computations of bone thickness and density point by point around the bone periphery and average values for the bone. The CT scanner system 10 provides 3D slice images of the object being scanned. These images are substantially planar. The bone thickness of the bone of interest is measured directly by the computer 12 which outputs as many as 100 or more data points about the bone periphery and automatically calculates the average thickness and density tables may also be produced showing the points measured. The operation of the CT scanner system 10 is conventional and need not be given herein.

The data generated from scanning are useful in cutting particular shaped implants from a given bone. They provide bone mineral density, known to correlate to strength, as well as dimensional values useful in determining bone that may be suitable and the type, shape and number of the final implants that can be optimally obtained from a given donor bone. Previously, this information was not directly available. Prior art such as fluoroscopy or other techniques known in the art, could not provide accurate data on a given bone because the image was two-dimensional and could not provide the actual shape of the bone of interest. These procedures required that assumptions be made about the geometry of the medullary canal and therefore was difficult to program and predict the shape and type of implant to be produced from a bone. Errors due to the projection and focus effects also introduced inaccuracies into the dimensional measurements of the two dimensional image of the bone.

Variants of computed tomography, including microcomputed tomography, computed tomography, peripheral computed tomography as well as additional three-dimensional imaging modalities (MRI, i.e., magnetic resonant imaging and so on) in commercially available instruments can also be used according to the present invention by appropriately programming such machines. In this procedure, scans from a limited number of transverse sites on a bone are used to predict suitability of a whole bone or bone fragment for production of implants for specific applications, e.g. scanning the mid-diaphyseal region of a femur allows the operator to assess the maximal cortical thickness of the bone, and to determine its suitability for grafts requiring wall thicknesses greater than a given size.

Figure 5A:
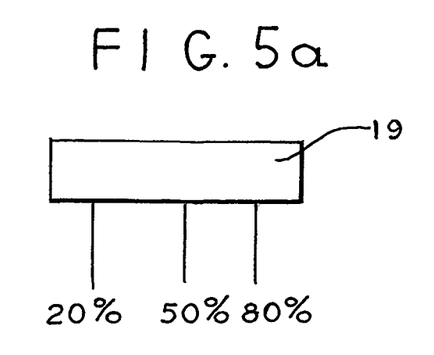
FIGS. 5a and 5b are respectively bone and packaged bone showing exemplary 3 scan positions relative to the bone while the bone is sealed in a double sealed package of FIG. 5b.
Figure 5B:
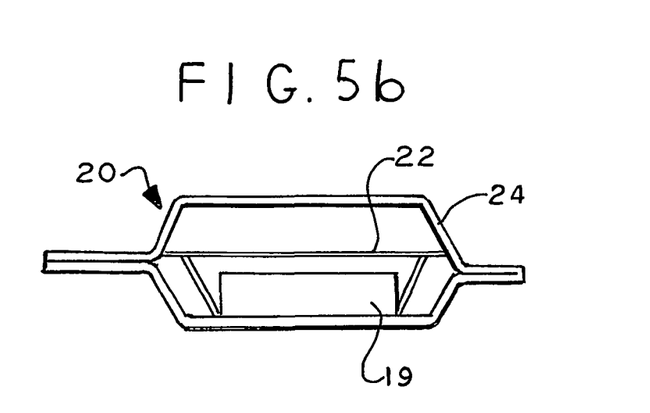

In a preferred embodiment, a high resolution imaging technique, CT scanning, is used to plan the processing of donor bone into a transplant graft implant In this process, representative sections of bones are scanned before the bone is processed and the images acquired for analysis. In FIG. 5a, for example, three positions are scanned as indicated at the 20%, 50% and 80% positions of the bone 19 of interest starting from the end of the bone. The positions 20%, 50% and 80% are calculated based on the overall length of the bone, or alternately, the "biomechanical length" of the bone, as described by Ruff (Ruff, C. B.: Structural Changes in the Lower Limb Bones With Aging at Pecos Pueblo, Ph.D. Dissertation, University of Pennsylvania, 1981. Ruff, C. B.: Allometry between length and cross-sectional dimensions of the femur and tibia in Homo sapiens sapiens. Am. J. Phys. Anthropol., 65: 347, 1984., both incorporated herein by reference) If time permits the entire bone may scanned and as technology improves the scan time for a whole bone will decrease. The bone is kept sterile in its original packaging 20 during scanning as shown in FIG. 5b. The package 20 comprises an inner package 22 and an outer package 24, both of which are thermoplastic material sealed with adhesives wherein the bone is sterile. A landmark identifier (not shown) found on or in the bone may also be used to place the scan positions if desired. This landmark may be a natural morphological site or detail of the bone such as fovea capitis, tip of the lesser trochanter, radial tuberosity, medial malleolus, etc., or an artificially added landmark such as a radiopaque pin or other radiopaque marker. The landmark identification is obtained by a lower resolution, rapid "scout scan" of the bone, after which the orientation of the bone in the scanner may be calculated by the computer program. This landmark may then be used to register or otherwise confirm the orientation of the bone in space, before cutting.

Figure 8:
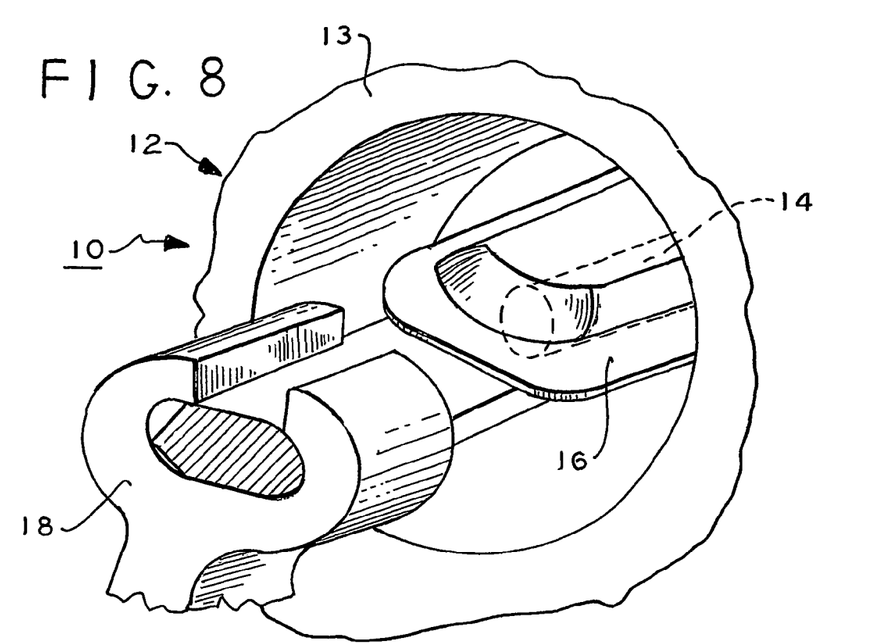
FIG. 8 is a more detailed isometric view of the CT scan apparatus of FIG. 1 for imaging a packaged bone.
Figure 10:
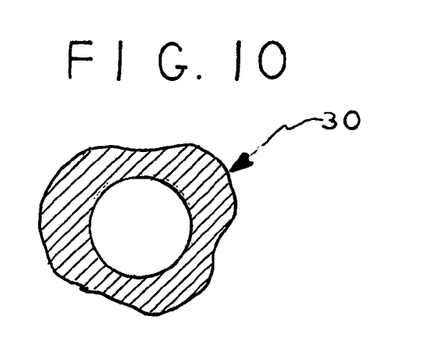
FIG. 10 is a diagrammatic representation of the scanned bone image as produced by the apparatus of FIG. 1.

In FIG. 8, a bone 14, which may be a section of a long bone, is sterile and contained in package 16 of the type defined above. A clamp fixture 18 holds and displaces the bone specimen in the imaging apparatus 13. In FIG. 10, a planar image 30 of bone 14 is generated. The system 10 automatically measures the dimensions of the bone thickness around its periphery as well as determining the bone density based on the software available in the CT scanning system 10.

Figure 9:
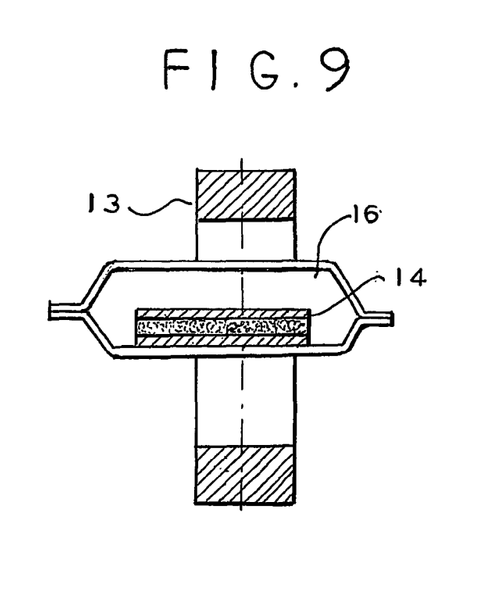
FIG. 9 is a sectional elevation view of the apparatus and packaged bone of FIG. 8.

The bone 14 is preferably frozen and in the original shipping packaging 16 at the time of scanning. The shipping packaging material typically consists of a sterile plastic sealed bag, surrounded by a cloth covering or wrap, taped securely, in a second outer wrap. Another advantage of using the current invention is that it does not require the frozen bone to be unwrapped (risking contamination) to scan and measure it. The bone may remain protected in the packaging during the entire process. FIG. 9. After scanning, the bone 14 in its package 16 it is preferably returned to cold storage, while the implant cutting plan, production plan, work order, or cutting specification is generated. When the planning process is complete, the bone 14 is thawed and processed at a predetermined scheduled time to produce the predetermined type and number of implants for a specific application.

All dimensions of all bones from a donor do not necessarily have to be scanned. The bones of a given donor have common properties and predictable dimensional relationships with each other. Therefore, only representative points such as the centers of one or more major long bones may be measured, and algorithms based upon experience, anthropometric relationships such as those described in, e.g. Steele D G, Bramblett C A. *The Anatomy and Biology of the Human Skeleton.* Texas A&M University Press. 291 pp., 1988, and Bass W. *Human Osteology* 3rd Edition, 1987, Missouri Archaeological Society incorporated herein by reference, or statistical or mathematical models relating the desired measurement or strength to a measured site, can be used to predict the yield of machined implants from the donor as a whole. Representative cancellous bone, such as a femoral head, can also be evaluated for density with the CT scanning system 10 and predictions made about the suitability of all the cancellous bone from that donor. The system 10 operates to provide information on both cancellous and cortical bone and can provide such information on a single bone being evaluated. Additionally the historical osteometric data generated from previous scans can be used as a basis for comparing the current bone being scanned. Based on the number and type of implants produced from similar bones in the past one can make very accurate estimations of the potential number and type of implants to be cut from a new, but similar bone. This reduces the time needed to make an implant cutting plan, production plan, work order, or cutting specification. Additionally a computer program may be utilized to optimize the quantity of grafts, meet the demand for specific graft shapes, reduce processing time, and cutting errors.

The choice of what implant product forms are to be made is heavily dependent on the anatomical characteristics of the bone, especially wall thickness and diameter of cortical bone, and density of cancellous bone. For producing machined, shaped implants from cortical shafts, it is necessary to know the bone canal internal diameter, outer diameter and wall thickness to at least an accuracy of +/−0.5 mm and preferably +/−0.2 mm or better. Such accuracy is provided by the system 10. For producing cancellous implants, the strength of the cancellous bone becomes important, which is correlated with density. Such density measurements are automatically produced by the CT scanner system 10. Therefore, density measurements can predict the suitability of cancellous bone to make weight bearing products for spinal fusion and other applications.

Measurement of dimensions and density is normally only possible as practiced in the prior art after the bone has been cut open since prior art radiographic techniques are inadequate for this purpose, which prior art techniques thus preclude preplanning. Once cut, it is best to process the bone to avoid the extra handling and potential deterioration that can result if the bone is refrozen. In an attempt to avoid this problem, various imaging techniques have been (and are still being) used but without satisfactory correlation to actual bone parameters. The goal is to fully assess the bone without having to cut it. However, prior art imaging techniques employ conventional X-Ray images that distort the bone image resulting in poor correlation of image measurements to actual dimensions of the specimen being measured.

Most prior art imaging techniques, however, have limitations that severely limit their usefulness. X-ray imaging (either film or fluoroscope) is sometimes employed for whole bone scans of tissue to check for hidden cysts and tumors. But the images are not accurate dimensionally to the extent needed to assess fully tissue dimensions in relation to processing needs in respect of bone implants which need to be accurately characterized as to strength, for example, for use as a spinal implant. Also, such apparatus do not and cannot produce automatically the required bone parameters as produced by the CT scanner system 10. There is typically distortion in the X-ray image due to point source of the radiation and the beam spreading that occurs with such X-ray beams means that the relative sizes of the bone images become distorted and are typically only accurate only within +/−1 to 2 mm. This is insufficient accuracy for processing spinal implants from a bone for example.

In addition, it is difficult especially to determine inner canal dimensions and wall thickness because the displayed image is a composite of the entire bone. Cross sections may be misinterpreted, if there is a portion of bone with an unusual density overlaying the image. Also, to obtain a full image of the wall thickness, it is necessary to rotate the bone and re-image it at each new, indexed position. To put the situation in perspective, minimum wall thicknesses of implants machined from cortical bone are in the range of 1.5 to 7 mm. X-ray images can be used to screen bone for potential products that can be made, but they cannot predict precisely the yield of implants. Classical X-ray imaging also cannot provide any form of quantitative density data.

DEXA (Dual Energy X-ray Absorptiometry) is an improved X-ray technique that uses twin X-ray beams. This gives reasonably quantitative average density data. The image is of the whole bone at once so information on density at different depths within the bone can only be obtained by multiple images taken at different rotational angles, and still the resolution is not perfect. In terms of fine dimensional measurements on cortical structures, DEXA suffers from the same limitations as conventional X-ray imaging techniques.

CT scanning uses X-rays to image bone, but by a more sophisticated means that allows precise 3-D imaging without significant distortion. This lets "slices" of bone be viewed from any angle and provides specific wall thickness, ID and OD measurements at the proper resolution to enable predictions of the bone suitable for cutting machined implants not possible with the prior art imaging apparatuses. In addition, precise measurements of cancellous bone density can be produced for accurately evaluating the cancellous strength. Useful modalities other than x-ray computed tomography also exist, including gamma ray computed tomography.

Magnetic resonance imaging is another technique that can provide 3-D information on bone. As MRI technology improves, allowing higher resolution, this approach becomes attractive as well.

The advantage of pre-evaluation of donor bone prior to processing is that the yield of useful implants and other tissue forms can be maximized. Donor tissue is a scarce resource and represents a very special gift. Therefore, any way of maximizing its usefulness is highly advantageous.

Figure 2A:
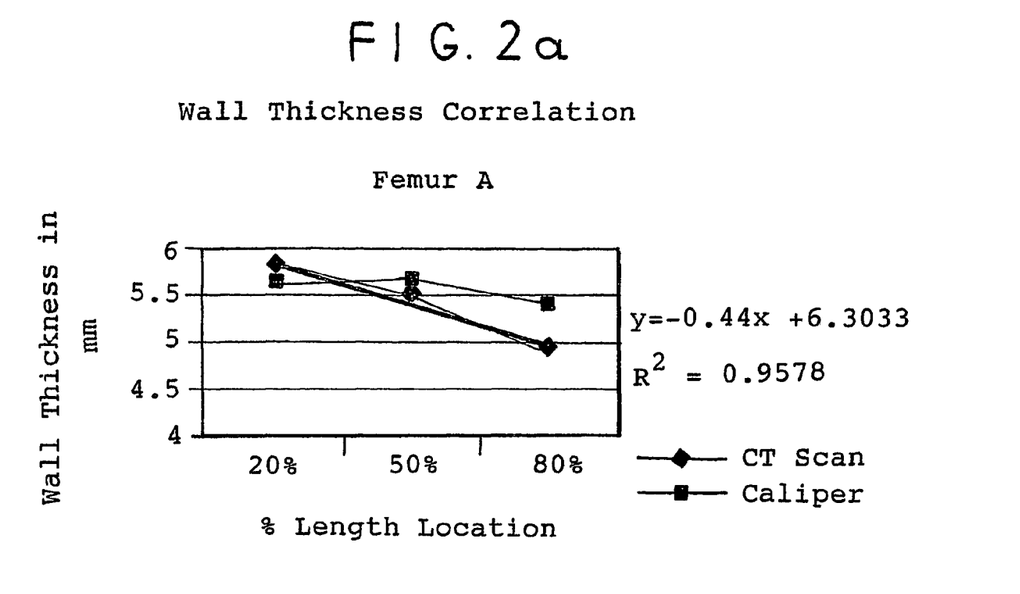
FIGS. 2a and 2b are graphs showing wall thickness correlation of a CT scanned bone images and caliper measurements for the same bone.
Figure 2B:
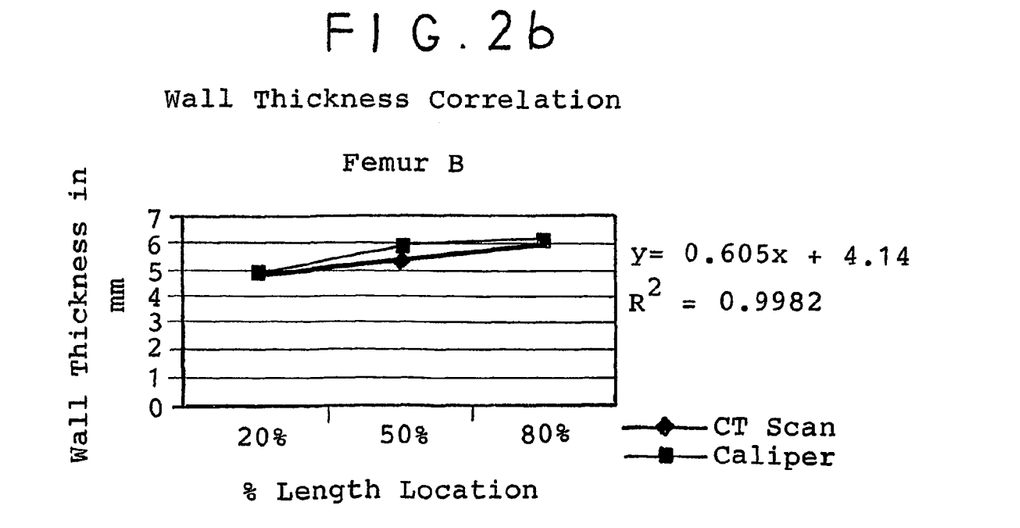

FIGS. 2a and 2b show wall thickness correlation of two specimens A and B. These show close correlation of the image scans to the measured caliper dimensions made on the specimen.

Figure 3:
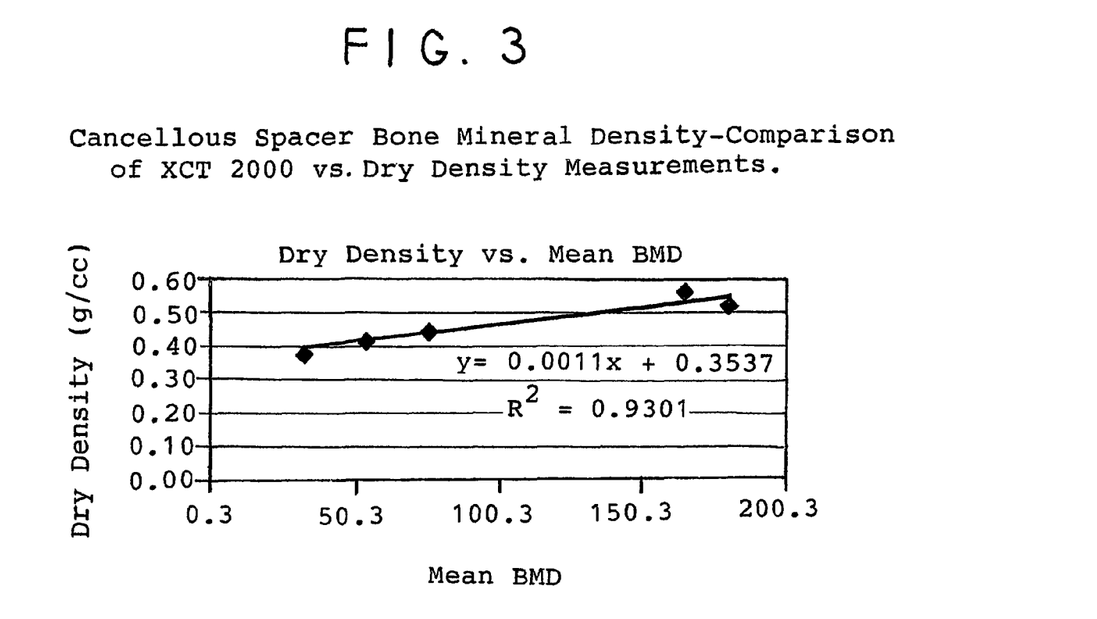
FIG. 3 is a graph showing a comparison of a CT measured cancellous bone block mineral density (BMD) to dry density.
Figure 4:
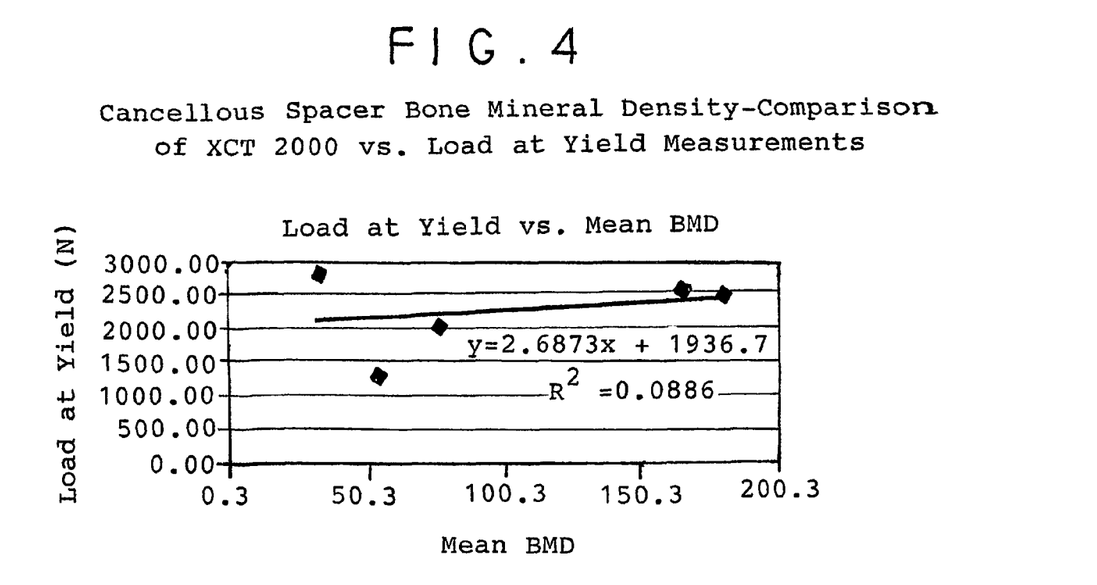
FIG. 4 is a graph showing a comparison of a CT measured cancellous bone block mineral density (BMD) to load at yield.

FIGS. 3 and 4 show the dry density vs. mean bone mineral density and load at yield vs. mean bone mineral density. The density values are in units of mg/cm3.

Figure 6:
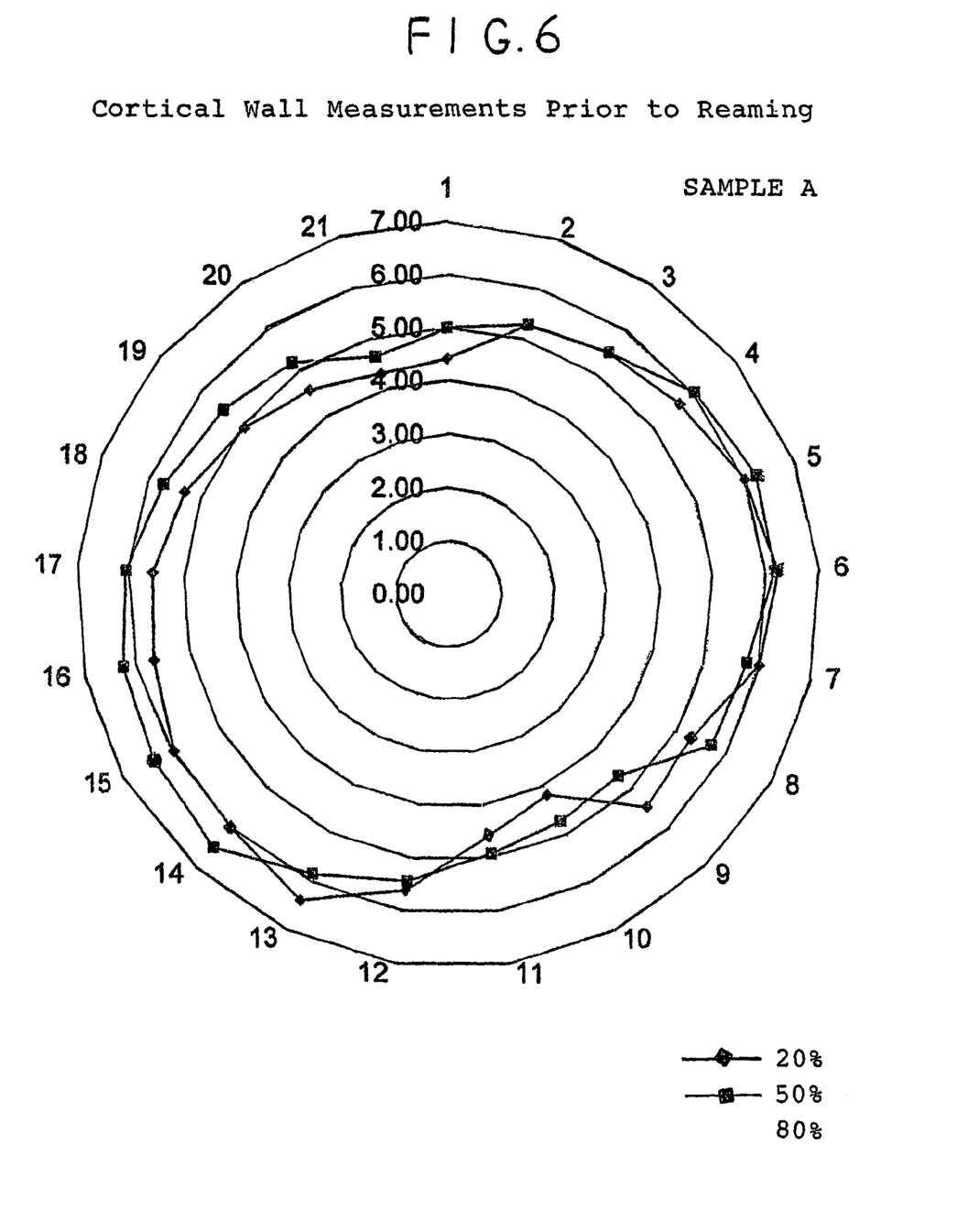
FIGS. 6 and 7 are plots of cortical bone measurements of two samples A and B prior to reaming the medullary canal at the 20% and 50% positions of the bone of FIGS. 5a and 5b.

FIG. 6 shows cortical wall measurements graph prior to reaming the central canal at the 20% and 50% positions, FIG. 5a.

Figure 7:
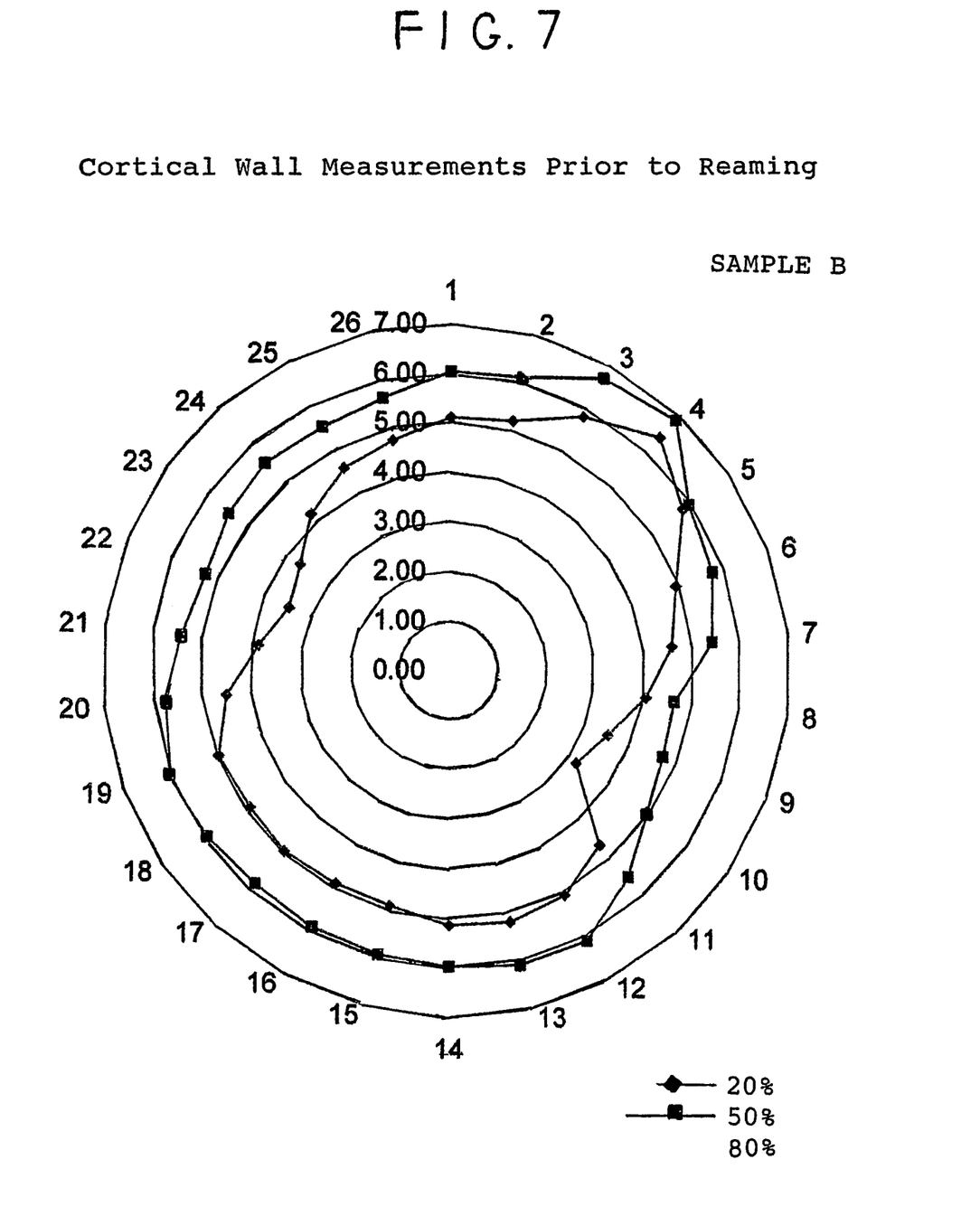

FIG. 7 is a graph of measurements made on bone sample B.

In FIG. 8, a bone 14, for example, a section of a donor long bone 14, is in its sterile package 16 as provided by the bone source. Various non-profit agencies provide such prepackaged donor bone. Such bones are then processed from rough bone sections into finished implants for use by a surgeon. The processed grafts are machined, cleaned using sterile techniques and/or sterilized and repackaged for end use by surgeons. The bone may be a complete long bone about 1-2 feet in length or long shafts with the ends removed or any partial segments. The bone sample imaging gives an accurate picture representation of the characteristics of the entire bone or fragment without having to image all of the bone.

The bone 14 is secured to a fixture 18, which then is used to place the bone in the scanner apparatus 12. The bone is located accurately in the scanner 12 imaging generator 13 by the fixture 18 which is attached to a movable table (not shown) which provides measured displacements of the bone from a reference position through the imaging generator 13 imaging space in a known manner.

In FIG. 10, the bone image, assuming a long bone, appears in cross section in a planar view. The scan provides the desired bone dimensions and density to provide accurate measurements of the cortical bone. These measurements are used to evaluate the bone for various implant configurations to be machined from that bone.

The present invention is directed to a process for evaluating donor bone suitability for processing as a particular implant configuration. In other words, employing 3 D imaging slices of the bone of interest and measuring density and cortical bone thickness to a high degree of precision, the bone can be fully evaluated as to dimensions and density for purpose of planning fabrication of a given implant configuration based on the evaluated bone. The 3 D images give more precise dimensioning and evaluation criteria for a given bone without destructive testing of the bone. Without such testing, it was not possible heretofore to accurately predict a particular bone's application for a given implant configuration to the desired accuracy needed.

The invention now will be described with respect to the following examples; however, the scope of the present invention is not intended to be limited thereby.

EXAMPLE 1

In performing the process of the present invention the following materials may be utilized.

Packaged Femur shaft, approximately 3 0mm in length
Packaged implants, aseptically processed and/or sterile.
pQCT XCT 2000 computed tomography scanning apparatus
Digital Caliper, calibrated Scale.

Sample measurements obtained by the pQCT XCT 2000 were highly correlated to measurements obtained using a calibrated caliper. $R^2$ values for samples Femur 'A' and 'B' were 0.957 and 0.998 respectively indicating excellent correlation. See FIGS. 2a and 2b.

Measurement locations were established based upon percent of length at 20%, 50% and 80% as described above. Three slices (approximately 2 mm apart) of each implant were taken. Average wall thickness data was outputted from the XCT 2000. Femur A and B were later cut into rings at the defined locations and then caliper readings were taken in 20-26 positions around the circumference of the ring prior to reaming. Average and sample statistics were calculated using Microsoft Excel.

The cycle time to perform the femur scan was 480 seconds for three slices+60 seconds for scout scan=540 seconds for each femur sample. When a fixture is used to hold multiple bones for scanning at the same time, this time is reduced substantially. Additionally, the resolution, slice thickness and number of slices assessed can be adjusted to achieve appropriate throughput on the system.

Average bone mineral density values obtained by the pQCT XCT 2000 were highly correlated to measurements obtained using a dry density method based on weight and size (also known as "apparent density method"). R-values for the five cancellous implants were 0.930 indicating excellent correlation. See FIG. 3.

Correlation to load yield or biomechanical yield strength was less strong, due primarily to one outlier data point. This may also be attributed to the inherent sample error for five samples. In addition, it was observed that one implant sample exhibited the lowest bone mineral density while exhibiting the highest biomechanical yield. Aside from sampling error, this may indicate that other factors not examined may contribute to biomechanical yield strength, e.g. internal cancellous architecture. The XCT 2000's technology is based upon in-vivo samples whereas the samples presented herein were processed and freeze dried. This requires measurement of additional samples to establish a "calibration curve" for the system. If one sample were omitted, the resulting R value would be 0.832 indicating a moderate correlation.

The cycle time to perform the implant scan was 680 seconds for three slices+60 seconds for scout scan=740 seconds for each cancellous implant sample.

It is desirable to interpolate the slice scans and generate an approximated 3D image for evaluation and to predict a cutting plan by implant type. In addition, the XCT 2000 system is capable of providing a full 3D image reconstruction of the object of interest although this requires additional cycle time to capture the information.

The measurement accuracy provided by the pQCT XCT 2000 of the imaged femur shaft closely approximates what is actually cut and measured. The bone mineral density provided by the pQCT XCT 2000 of the imaged cancellous implants through the package correlates with the apparent density measurement and biomechanical yield strength. The slice data for the imaged femur shaft allows for an implant cutting plan to specify implant type and expected quantity that will closely approximate the actual output cut from the tissue and correlate with the 3D reconstruction output from the pQCT XCT 2000.

To provide comparable data, and a consistent sampling site in donor bones of a variety of sizes, the method of the invention employs measurements at specific locations along the length of the shaft. A preferable site for measurement is 50% of the measured length of the bone.

Density values for the implants will be lower if measured with the marrow intact.

For the femur specimens there are other parameters that can be noted. The density (cortical) of the specimens at the selected scan slices was approximately 1200 mg/cm3 (as expected). Area values may also be reported.

In terms of generating a 3D rendering of a specimen, the following is considered. First, the XCT 2000 scanner can acquire up to 99 images based on a scanning protocol (scan slices defined on the scout scan for example). The file format for the individual slices will be identical. It depends on the software to take the individual slices and render them into 3D. In practice, 99 slices 2 mm apart will cover the extent of a femur 200-220 mm long. Such a scan program will take 1.5 to 2 hrs to complete.

It is preferred that all scan slices are to be a no more than of 2.2 mm thick. Slice locations are preferably as defined and shown above to provide consistent results. Each implant should be scanned through an existing sealed package.

Preferably, upon the creation of a 3D image of the femur shafts from the scan, a cutting plan is then prepared. Femur Shafts x-rayed using a Faxitron unit may be assessed for cortical thickness using this technology as a comparison to the pQCT XCT 2000. The process also may employ cutting the femur shafts and measuring the cortical thickness using a calibrated caliper. The femur shaft is processed according to the cutting plan and the output compared to the cutting plan prediction to ascertain the correlation of the plan to the results.

EXAMPLE 2

A femur specimen is scanned at three measurement locations based upon percent of length at 20%, 50% and 80% as described above. Three slices (approximately 2 mm apart) of each location are taken and the cortical thickness, interior diameter (ID) and outer diameter (OD) dimensions, density of the donor cortical and cancellous regions of the bone are measured. These values are then compared to an archive of at least 100 previous bone scans for comparison, or a statistical regression or alternatively a multivariate or mathematical model summarizing these measurements. A computer matrix compares the current bone scan information to the collected osteometric data, based on bones which were previously scanned and cut into implants. This matrix contains the three-dimensional morphometric measurements of the previous bones, including cortical thickness, interior diameter (ID) and outer diameter (OD) dimensions, density of the donor cortical and cancellous regions of the bone. It also contains information about the quantity and type of implants, which were cut from each bone in the past as well as the specific implant geometries (such as height, length and width etc.) might also contain and biomechanical requirements (such as mechanical strength). A separate, sourcing the matrix contains information on the number of grafts, which are currently needed or ordered, as well as templates for making the grafts. This analytical program could also be a neural network, used to "train" on which bone characteristics produce which types of implants. The computer compares the results of the three scanned regions to the stored osteometric data and the current implants needed, to determine the best implant cutting plan and optimum for that particular bone. The end result is an implant cutting plan based on the assessment of three dimensional morphometric measurements, which provides data on the fabrication of a given implant configuration based on the measured parameters. After implants have been cut from the bone, data related to the actual implant yield are recorded in the computer program to increase the number of bone scans used in future comparisons. This provides increasingly more accurate estimations of a bone's suitability for making various implants as the sample size increases.

While various embodiments of the present invention have been described, it will occur to those of ordinary skill that various modifications may be made to the disclosed embodiments. It is intended that the scope of the invention be as defined in the appended claims.

REFERENCE

Technical Reference: Chapter 19, "Computed Tomography", pp. 289-322, Christiansen's Physics of Diagnostic Radiology, 4th edition, Currey, Dowdey and Murry, eds, Lea & Febiger, Philadelphia, 1990.

What is claimed is:

1. A process for evaluating donor bone suitable for implant preparation comprising:
   a. non-destructively imaging a donor bone, prior to implantation, using a three-dimensional imaging scan at one or more sites of the bone;
   b. measuring parameters of the donor bone from the scan image, wherein the measured parameters include measurements chosen from a group consisting of bone volume, bone density, mineral density, and size and position of a canal;
   c. assessing, by a processor, the donor bone's suitability for fabrication into a given implant configuration based on the measured parameters; and
   d. cutting the donor bone into at least one implant if the donor bone is assessed to be suitable for fabrication into the given implant configuration based on the measured parameters.

2. The process of claim 1 wherein the donor bone is registered or oriented in space before cutting.

3. The process of claim 1 wherein the implant configuration is marked on the donor bone.

4. The process of claim 1, and further comprising:
   formulating, by the processor, an implant cutting plan after assessing the donor bone's suitability for fabrication into a given implant configuration based on the measured parameters.

5. The process of claim 4 wherein the donor bone is cut into a plurality of implants based on the implant cutting plan.

6. The process of claim 4 where the cutting plan is formulated from a computer based model.

7. The process of claim 6 where the model is scalable.

8. The process of claim 5 wherein the donor bone is cut manually.

9. The process of claim 5 wherein the donor bone is cut by an automated device.

10. The process of claim 1 wherein the imaging step comprises scanning by computed tomography.

11. The process of claim 1 wherein the imaging step comprises scanning by peripheral computed tomography.

12. The process of claim 1 wherein the imaging step comprises scanning by magnetic resonance imaging.

13. The process of claim 1 wherein the imaging step comprises scanning by gamma-ray computed tomography.

14. A process for evaluating donor bone suitability for implant preparation, comprising:
   a. non-destructively imaging the donor bone, prior to implantation, using three-dimensional image scanning at one or more sites on the donor bone to obtain at least one scan image of the donor bone;
   b. measuring parameters of the donor bone from the at least one scan image, wherein the measured parameters include measurements of bone volume, bone density, mineral density, and size and position of a canal;
   c. extrapolating from morphometric measurements to dimensions at another skeletal site on the same or another bone;
   d. determining, by a processor, the donor bone's suitability for fabrication into a given implant configuration based upon extrapolated implant geometries and the measured parameters; and
   e. cutting the donor bone into at least one implant if the donor bone is determined to be suitable for fabrication into the given implant configuration based on at least one of the extrapolated implant geometries and the measured parameters.

15. The process of claim 14, and further comprising: marking an implant configuration on the donor bone.

16. The process of claim 14, and further comprising: formulating, by the processor, an implant cutting plan after determining the donor bone's suitability for fabrication into the given implant.

17. The process of claim 15 wherein the donor bone is cut into a plurality of implants based on both the extrapolated implant geometries and the measured parameters.

18. The process of claim 17 wherein the donor bone is cut manually.

19. The process of claim 17 wherein the donor bone is cut by a computer assisted device.

20. The process of claim 14 wherein the imaging step comprises producing the image by computed tomography.

21. The process of claim 14 wherein the imaging step comprises producing the image by peripheral computed tomography.

22. The process of claim 14 wherein the imaging step comprises producing the image by magnetic resonance imaging.

23. The process of claim 14 wherein the imaging step comprises producing the image by gamma-ray computed tomography.

24. A process for evaluating, by a processor, donor bone suitability for implant preparation comprising:
   non-destructively assessing cortical thickness at one or more preselected sites of the donor bone prior to implantation;
   storing or writing the assessed cortical thickness in computer memory;
   determining, by the processor, the donor bone's suitability for fabrication into a given implant configuration based upon the assessed cortical thickness; and
   cutting the donor bone into at least one implant if the donor bone is determined to be suitable for fabrication into the given implant configuration based on the assessed cortical thickness.

25. The process of claim 24 including measuring the donor bone to within +/−0.005 mm accuracy.

26. The process of claim 24 including measuring the donor bone to within +/−0.01 mm accuracy.

27. The process of claim 24 including measuring the donor bone to within +/−0.1 mm accuracy.

28. The process of claim 24 including measuring the donor bone to within +/−0.5 mm accuracy.

29. The Process of claim 24 including measuring the donor bone to within +/−1.0 mm accuracy.

30. The process of claim 1 wherein said process is employed as a method for determining critical attributes of bone related to predetermined release specifications for the bone for either processing or final product specifications.

31. The process of claim 14 wherein said process is employed as a method for determining critical attributes of bone related to predetermined release specifications for the bone for either processing or final product specifications.

32. A method of formulating a bone implant cutting plan, comprising:
   non-destructively assessing, by a processor, the three-dimensional morphometric measurements of a donor bone, prior to implantation;
   measuring parameters of the donor bone including bone density and mineral density;
   assessing the donor bone's suitability for fabrication into a given implant configuration based on the three-dimensional morphometric measurements and the measured parameters;
   formulating the cutting plan if the done bone is assessed to be suitable for fabrication into the given implant configuration; and
   cutting the donor bone into at least one implant based on the cutting plan,
   wherein said cutting plan identifies cutting locations on said donor bone, and said cutting plan is stored in computer memory or used to generate a work order.

33. The method of claim 32 wherein said three-dimensional morphometric measurements are derived from a model selected from the group consisting of a mathematical model, a statistical model, a neural network model, and a computer model.

34. The method of claim 32 wherein said cutting plan identifies bone which may be processed to provide a subset of bone implants having one or more specified dimensional, strength, or physical characteristics.

35. The method of claim 32 wherein said cutting plan identifies dimensions and shapes which may be obtained from the donor bone having specified morphometric measurements.

36. A method for processing donor bone for implantation comprising:
   a. non-destructively assessing and imaging a donor bone, prior to implantation, using a three-dimensional imaging scan at one or more sites of the bone;
   b. measuring parameters of the donor bone from the scan image, wherein the measured parameters include measurements chosen from a group consisting of bone volume, bone density, mineral density, and size and position of a canal;
   c. assessing, by a processor, the donor bone's suitability for fabrication into a given implant configuration based on the measured parameters;
   d. formulating, by the processor, an implant cutting plan if the donor bone is assessed to be suitable for fabrication into the given implant configuration based on the measured parameters; and
   e. cutting the donor bone into multiple implants based on the implant cutting plan.

* * * * *